(12) United States Patent
Platzek et al.

(10) Patent No.: US 7,181,956 B2
(45) Date of Patent: Feb. 27, 2007

(54) RHEOMETER

(75) Inventors: Wolfgang Platzek, Karlsruhe (DE);
Joachim Faust, Keltern-Weiler (DE)

(73) Assignee: Thermo Electron (Karlsruhe) GmbH, Karlsruhe (DE)

( * ) Notice: Subject to any disclaimer, the term of this patent is extended or adjusted under 35 U.S.C. 154(b) by 0 days.

(21) Appl. No.: 11/244,186

(22) Filed: Oct. 6, 2005

(65) Prior Publication Data
US 2006/0081037 A1    Apr. 20, 2006

(30) Foreign Application Priority Data
Oct. 16, 2004    (DE)    ............ 10 2004 050 753

(51) Int. Cl.
*G01N 11/14*    (2006.01)
(52) U.S. Cl. .................................. 73/54.31
(58) Field of Classification Search .............. 73/54.28, 73/54.23, 54.37, 54.39, 54.31, 846, 856, 73/859, 860
See application file for complete search history.

(56) References Cited

U.S. PATENT DOCUMENTS 4,535,621 A * 8/1985 Gervais et al. ............ 73/54.23

* cited by examiner

*Primary Examiner*—Hezron Williams
*Assistant Examiner*—Tamiko Bellamy
(74) *Attorney, Agent, or Firm*—Paul Vincent

(57) ABSTRACT

A rheometer has a measuring shaft which is borne for rotation about and/or axial displacement along its longitudinal axis and has a detection device for determination of the normal force and/or the torque which acts on the measuring shaft during a measurement. The detection device thereby has a first holding member which is connected to the measuring shaft and a second holding member which is mounted to a stationary frame, wherein the second holding member is connected to the first holding member by means of resilient connecting members and at least one strain gage is introduced onto at least one of the connecting members to measure the deformation of the connecting member.

8 Claims, 2 Drawing Sheets

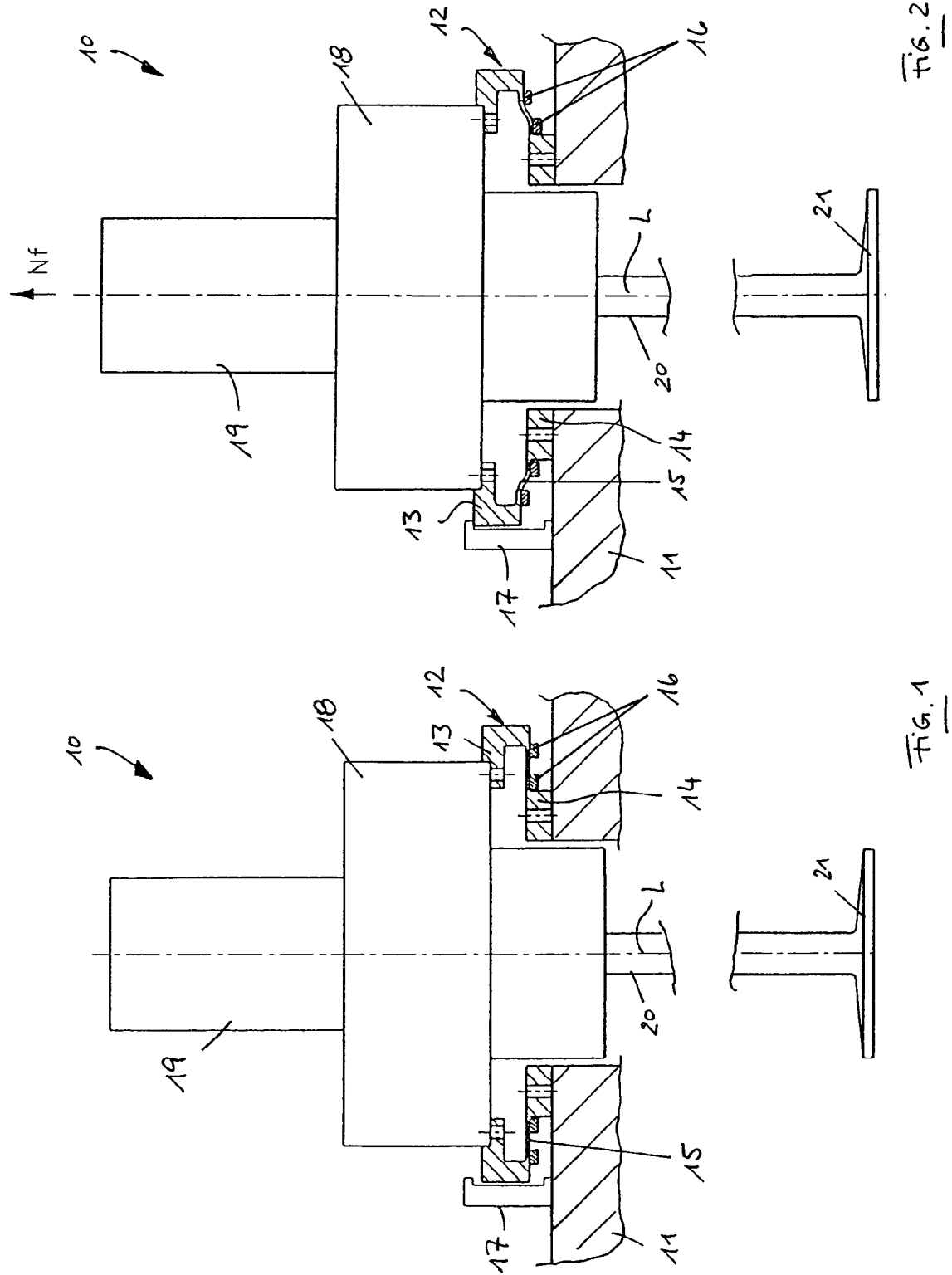

RHEOMETER

This application claims Paris Convention priority of DE 10 2004 050 753.8 filed Oct. 16, 2004 the complete disclosure of which is hereby incorporated by reference.

BACKGROUND OF THE INVENTION

The invention concerns a rheometer having a measuring shaft which is borne for rotation about and/or axial displacement along its longitudinal axis and with a measuring device for measuring the normal forces and/or the torque which acts on the measuring shaft during the measurement.

The measuring of rheological quantities of a material using a rheometer is based on the precise knowledge of the relationship between the tensile forces and the deformation of the material. In order to extract the material properties from these characteristic dependencies it is necessary to measure the tensile force and the deformation of a material sample in as precise a manner as possible. The sample is disposed between two plate-shaped measurement components, with one of the measuring components being connected to a driven measuring shaft by means of which a shearing force can be introduced onto the sample. During the measurement, an additional normal force acts on the measuring shaft as well as a resulting torque about the axis of the measurement shaft, both of which depend on the material in the sample and are measured and utilized to determine the material characteristics.

In former times, it was customary to bear the measuring shaft on an apparatus housing using springs and to determine the deformation of the springs during the course of the measurement. The deformation of the springs, together with the knowledge of the stiffness of the spring and/or of the spring constant were used to determine the normal forces and the resulting torques. In more modern rheometers, the displacement of the measuring shaft is determined either using optical procedures while taking advantage of the refraction of light in a narrow gap or by making use of electro-capacitive techniques. Both procedures are difficult from a technical point of view and, in particular with respect to the optical procedures, are limited with respect to their precision.

It is the underlying purpose of the invention to introduce a rheometer of the above mentioned kind with which the normal forces and/or the torques on the measuring shaft can be determined in a straightforward fashion.

SUMMARY OF THE INVENTION

This purpose is achieved in accordance with the invention using a rheometer having the features of the independent claim. Towards this end, the measuring device has a first holding member which is connected to the measuring shaft and a second holding member which is mounted in a stationary fashion to a frame, wherein the second holding member is connected to the first holding member by means of resilient connecting members and a strain gage is introduced on at least one of the connecting members to determine the deformation of the connecting member.

Strain gages (sometimes referred to as wire and/or resistive strain gages) have been known for some time in measurement technology. In accordance with the invention, these strain gages are used to determine the normal force and/or the resulting torque on a measuring shaft in a rheometer by introducing the strain gages at defined positions, namely on the connecting members between the two holding members. Evaluation of the data extracted from the strain gages is done in a conventional fashion, so that no further discussion of this procedure is required at this point.

A plurality of connecting members are preferentially provided between the two holding members and are, in particular, evenly distributed about the periphery of the measuring shaft. It has turned out to be advantageous for each of the connecting members to have one, single strain gage so that possible misalignments of the measuring shaft can be reliably determined and taken into consideration when calculating the characteristic values.

In a preferred configuration of the invention, the holding member is formed from concentrically distributed rings and the connecting members are radial bridges connecting the rings. The holding members can be preferentially configured as an integral part together with the connecting members as a monolithic piece which, in particular, is made from a deformable metal such as aluminum.

The bridges are preferentially configured as plates oriented in such a fashion that their smallest dimension extends in the measuring direction e.g. for measurement of the normal force, along the longitudinal direction of the measuring shaft, and for measurement of the torque, tangential to the longitudinal direction of the measuring shaft.

The bridges are preferentially distributed evenly about the periphery of the ring shaped holding members, wherein either four bridges displaced with respect to each other by 90 degrees, or six bridges displaced with respect to each other by 60 degrees can be provided.

In order to avoid damage or plastic deformation of the bridges in the event of excessively large normal forces or torques, an improvement of the invention provides for a limiting device which limits the relative motion between the holding members to a predetermined amount to thereby guarantee that the bridges are always subject to an elastic deformation within the "Hookes" region of the material characteristic dependence, and subsequently return to their original position.

A particularly simple configuration of the limiting members is given when these are configured as stops, wherein the stops can be formed on one of the holding members and can cooperate with stop elements which are present on the other holding member.

Further details and features of the invention can be extracted from the following description of embodiments while taking into consideration the drawings.

BRIEF DESCRIPTION OF THE DRAWING

FIG. 1 shows a schematic side view of the bearing of the measurement shaft in a initial state;

FIG. 2 shows a representation corresponding to that of FIG. 1 under axial displacement of the measuring shaft in response to a normal force;

DESCRIPTION OF THE PREFERRED EMBODIMENT

Figure 3:
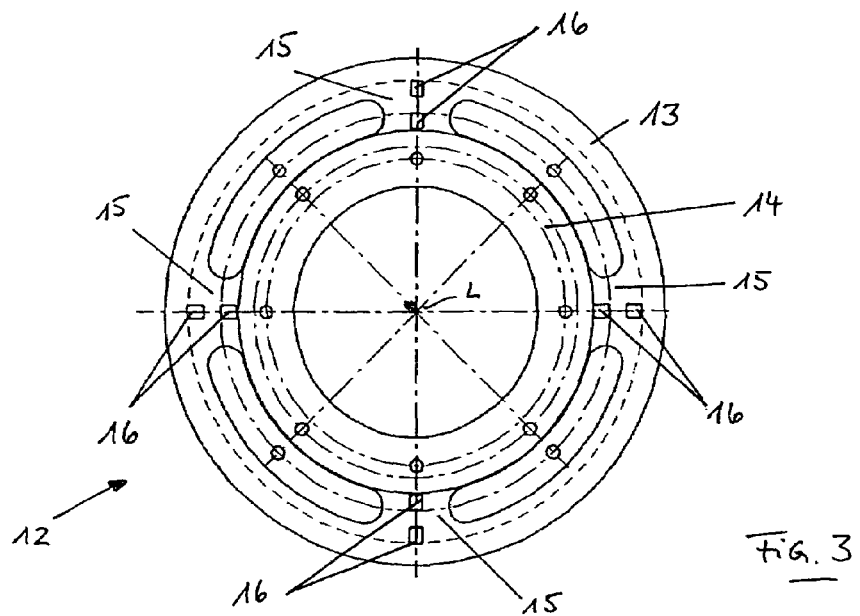
FIG. 3 shows a plan view onto the measuring device used in the configuration according to FIGS. 1 and 2.

FIG. 1 shows a rheometer measuring shaft which bears a plate-shaped measuring member 21 at its lower end which seats on a material sample (not shown). The measuring shaft extends in a substantially vertical direction and, at its upper end, bears a measuring head 18 on which a rotational drive 19 for a measuring shaft 20 is mounted. The measuring shaft 20 can be rotated about its vertical longitudinal axis L by means of the rotational drive 19.

The measuring shaft 20 is borne via the measuring head 18 on a detection device 12 which has a first ring shaped holding member 13 connected to the measuring head 18 and is disposed coaxially with respect to the longitudinal axis L of the measuring shaft 20. The detection device 12 also includes a second ring-shaped holding member 14 which is disposed coaxially with respect to the first ring shaped holding member 13 and is rigidly mounted to a frame 11 of the rheometer 10, wherein mounting-related strains and stresses are avoided. The two ring-shaped holding members 13 and 14 are connected by four radial bridges 15 which are evenly distributed about the periphery of the measuring device 12 with mutual displacements of 90 degrees (see FIG. 3). The bridges 15 have a very small extension in the longitudinal direction of the measuring shaft 20 and constitute resilient connecting members between the two ring-shaped holding members 13 and 14. At least one strain gage 16 is securely attached to each bridge 15 to measure the elastic deformation of the corresponding bridge 15.

The first ring-shaped holding member 13 has an associated stop 17 with which the first ring-shaped holding member 13 can come in abutment as soon as a predetermined relative motion with respect to the frame fixed second ring-shaped holding member 14 occurs.

FIG. 1 shows the initial state of rheometer 10 with which the measuring shaft 20 is not subjected to load and the first ring-shaped holding member 13 is not in abutment with the stop 17.

In accordance with FIG. 2, a vertically directed normal force $N_F$ is acts on the measuring shaft 20 in the longitudinal direction L during the course of a measurement and the measuring head 18 is lifted, together with the first ring-shaped holding member 13, away from the second ring-shaped holding member 14 under elastic deformation of the bridges 15. FIG. 2 shows the end position in which the first ring-shaped holding member 13 abuts the upper end of the stop 17. The elastic deformation of the bridges 15 can be determined by the strain gage 16 and evaluated in a conventional fashion. As soon as the normal force $N_F$ no longer acts on the measuring shaft 20, the measuring shaft 20 along with the measuring head 18 and the first ring-shaped holding members 13 returns to the original configuration shown in FIG. 1 in response to the elastic restoring forces of the bridges 15.

Figure 4:
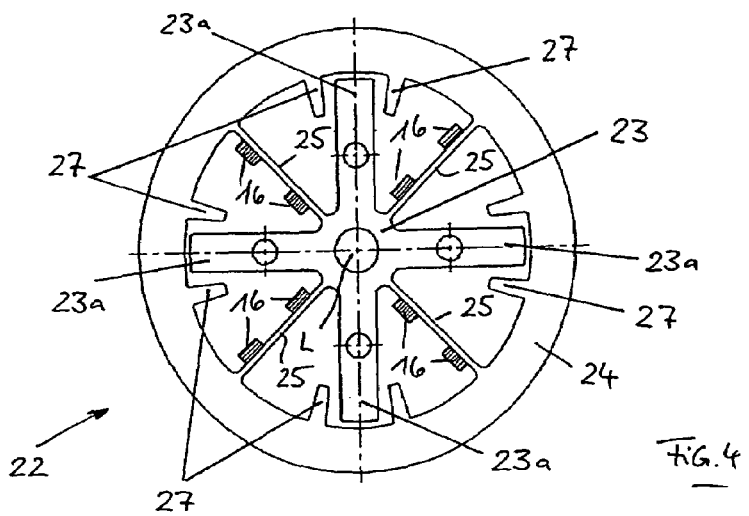
FIG. 4 shows a plan view of an alternative measuring device for determining the torque of the measuring shaft in an initial state.
Figure 5:
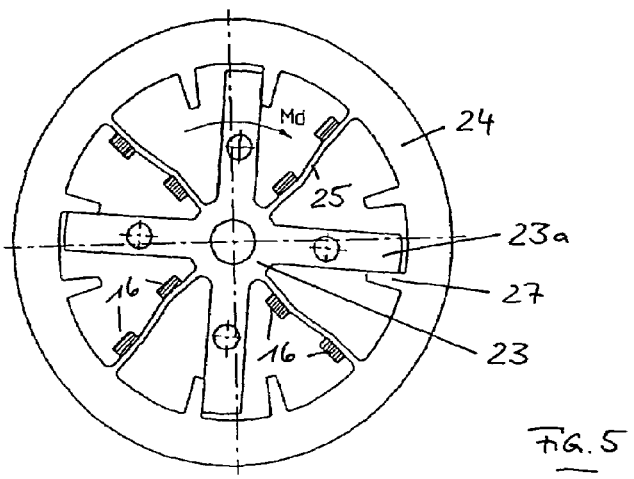
FIG. 5 shows a representation corresponding to that of FIG. 4 in response to a torque on the measuring shaft.

FIGS. 1, 2 and 3 illustrate measurement of normal forces $N_F$ on the measuring shaft 20. FIGS. 4 and 5 show a detection device 22 with which the torque on the measuring shaft 20 can be determined. The detection device 22 includes a first ring-shaped holding member 23 which is disposed coaxially with respect to the longitudinal axis L of the measuring shaft 20 and has four radially outwardly protruding cross-shaped stop fingers 23a on which (in a manner not shown in greater detail) the measuring head is mounted for secure mutual rotation along with the measuring shaft while avoiding excessive stresses and strains. A detailed view of the measuring head and the measuring shaft is not shown in FIGS. 4 and 5, since these have the construction already illustrated in FIGS. 1 and 2.

Four radial bridges 25 are evenly distributed, with mutual respective displacements of 90 degrees, about the periphery of a first ring-shaped holding member 23 and connect to an outer concentrically disposed second ring-shaped holding member 24 which is mounted in a fixed manner with respect to the frame of the rheometer. The bridges 25 are plate-like, with the plane of each plate extending in a direction of the longitudinal axis L of the measuring shaft i.e. the normals to the planes of the plates are substantially tangential to the longitudinal axis of the measuring shaft. In this manner, the two ring-shaped holding members 23 and 24 can be rotated relative to each other under elastic deformation of the bridges 25 in the peripheral direction of the measuring shaft. Strain gages 16 are introduced on each bridge 25 and are connected in a conventional fashion, not described in greater detail, to a conventional analysis device (not shown).

Stops 27 are disposed on the inner side of the outer second ring-shaped holding member 24 facing the first ring-shaped holding member 23 with each stop finger 23a of the first ring-shaped holding member 23 having two associated stops 27. A free end of the corresponding stop fingers 23a is disposed with play between the two stops 27.

A torque Md acting on the measuring shaft 20 causes rotation of the measuring head as well as of the first ring-shaped holding member 23 about the longitudinal axis L of the measuring shaft 20 and an elastic deformation of the bridges 25 occurs, as shown in FIG. 5. This elastic deformation of the bridges 25 is measured by the strain gages 16 disposed on the bridges 25 and is introduced in a conventional fashion to an evaluation means. The relative rotation between the first ring-shaped holding member 23 and the second ring-shaped holding member 24 is limited by abutment of the stop fingers 23d on the stops 27, as shown in FIG. 5.

We claim:

1. A rheometer comprising:
   a frame;
   a measuring shaft borne for rotation about and/or axial displacement along a longitudinal axis thereof;
   a first holding member connected to said measuring shaft;
   a second holding member connected to said frame;
   resilient connecting members connected between said first holding member and said second holding member; and
   at least one strain gage cooperating with at least one connecting member to measure a deformation thereof, said first holding member, said second holding member, said connecting members and said at least one strain gage defining a detection device for measuring a normal force and/or a torque acting on said measuring shaft.

2. The rheometer of claim 1, wherein each connecting member has one strain gage.

3. The rheometer of claim 1, wherein said first and said second holding members are formed by concentrically disposed rings, wherein said connecting members are radial bridges connecting said rings.

4. The rheometer of claim 3, wherein said bridges are evenly distributed about rims of said ring-shaped first and second holding members.

5. The rheometer of claim 1, wherein said first holding member, said second holding member, and said connecting members are integral with each other.

6. The rheometer of claim 1, further comprising means for limiting a relative motion between said first and said second holding members.

7. The rheometer of claim 6, wherein said limiting means comprises stops.

8. The rheometer of claim 7, wherein said stops are formed on one of said first and said second holding member and cooperate with stop elements which are formed on another one of said first and said second holding members.

* * * * *